United States Patent [19]

Judet

[11] Patent Number: 5,314,485

[45] Date of Patent: May 24, 1994

[54] TOTAL PROSTHESIS OF THE WRIST

[75] Inventor: Thierry Judet, Ville d'Avray, France

[73] Assignee: Etablissements Tornier, Saint-Ismier, France

[21] Appl. No.: 943,565

[22] Filed: Sep. 11, 1992

[30] Foreign Application Priority Data

Sep. 12, 1991 [FR] France ............................ 91 11465

[51] Int. Cl.$^5$ ............................ A61F 2/42; A61F 2/30
[52] U.S. Cl. ............................ 623/21; 623/18
[58] Field of Search ............................ 623/21, 18, 16

[56] References Cited

U.S. PATENT DOCUMENTS

| | | | |
|---|---|---|---|
| 4,021,864 | 5/1977 | Waugh | 3/1.91 |
| 4,040,130 | 8/1977 | Laure | 3/1.91 |
| 4,106,128 | 8/1978 | Greenwald et al. | 623/21 |
| 4,213,208 | 7/1980 | Marne | 623/21 |
| 4,259,752 | 4/1981 | Taleisnik | 3/1.91 |
| 4,307,473 | 12/1981 | Weber | 3/1.91 |
| 4,784,661 | 11/1988 | Beckenbaugh et al. | 623/21 |

FOREIGN PATENT DOCUMENTS 1412376 4/1973 United Kingdom ............ A61F 1/00

*Primary Examiner*—Randall L. Green
*Assistant Examiner*—Dinh X. Nguyen
*Attorney, Agent, or Firm*—Dowell & Dowell

[57] ABSTRACT

A total wrist prosthesis with a radio-carpal articular level having a first radio-ulnar center of rotation located in a frontal plane and a medio-carpal articular level having a second radio-ulnar center of rotation located also in the frontal plane but being distinct from the first radio-ulnar center of rotation. The prosthesis including a radial element having an anchoring shank insertable into the distal portion of a radius bone, and a shoulder resting against the distal face of the said radius bone. A plate is connected to the radial element having a concave bearing surface having a radio-ulnar deviation radius of curvature in the frontal plane and a flexion-extension radius of curvature in a sagittal plane smaller than the radio-ulnar deviation radius of curvature. An intermediate element is also provided rotatable in radio-ulnar deviation and in flexion-extension with respect to the concave bearing surface and having a shape so as to cooperate with the concave bearing surface, and including a recess offset dorsally and in an ulnar direction. A metacarpal element is provided for anchoring into metacarpal bones and is free to rotate solely in a radio-ulnar deviation movement with respect to the intermediate element.

3 Claims, 3 Drawing Sheets

TOTAL PROSTHESIS OF THE WRIST

BACKGROUND OF THE INVENTION

1. Field of the Invention

The present invention relates to a total prosthesis of the wrist which comprises means for mechanically reproducing the kinematics of a healthy wrist.

2. History of the Related Art

Prostheses of this type are known, which more generally comprise a block of elastic material made, for example, of a matter called "SILASTIC". Such prostheses are not correctly adapted to the osseous environment, while their design remains a rudimentary approach to the kinematics of the wrist.

In addition, other prostheses are made of metal, assimilating the wrist to a spherical articulation thereby not allowing normal kinematics and consequently limiting the function of the wrist.

U.S. Pat. No. 4,307,473 also discloses prostheses which comprise three elements each having distinct slide surfaces for the radio-cubital movements of flexion-extension and of deviation. These slide surfaces have certain drawbacks as they are limited in their degrees of freedom and are only centered at a single point. This prevents reproduction of the normal kinematics of a healthy wrist.

SUMMARY OF THE INVENTION

The present invention intends to overcome these drawbacks. The invention has the object of producing a total prosthesis of the wrist comprising three distinct elements. These elements are assembled with the osseous, ligamentous and muscular structures remaining in place to guide the movement of the wrist without subjecting the implant to stresses which risk handicapping the patient.

In addition, the three elements offer distinct centers of rotation for the two principal movements of the wrist, while the intermediate element, or second element, is totally free to rotate in two perpendicular planes, allowing radio-ulnar and dorso-palmar displacement of the medio-carpal articular center during the movement.

To that end, the total prosthesis of the wrist includes an element, and more particularly the second or intermediate element, which has at least two different centers of curvature of which one lies in the anatomic sagittal plane, while the other is provided in the anatomic frontal plane so as to reproduce, respectively, a rotation in flexion-extension and a rotation in radio-ulnar deviation.

The total prosthesis of the wrist according to the present invention thus comprises:

a first element fixed in the distal radial diaphysis and including an anchoring shank, of elongated form, adapted to the internal morphology of the radius and a plate attached to the shank which abuts against the osseous section of the radius and which is covered with a plate of bio-compatible plastic material which has a concave outer surface along its two principal axes;

a second element free to rotate in all the planes with respect to the first element, which replaces the lunate and scaphoid bones in order to effect radiocarpal rotations of the wrist. The second element is in the form of a conical barrel so as to cooperate with the concave surface of the plate. The barrel, in the frontal plane, is defined by an arc of a circle having a radius greater than that provided in the sagittal plane and a recess offset in the ulnar direction of the frontal plane and in the dorsal direction of the sagittal plane;

and a third element free to rotate in the frontal plane with respect to the second element and being anchored in the metacarpals of a hand, thereby ensuring the medio-carpal rotation of the wrist.

BRIEF DESCRIPTION OF THE DRAWINGS

The accompanying drawings, given as an example, will enable the invention, the characteristics that it presents and the advantages that it is capable of procuring, to be more readily understood.

DESCRIPTION OF THE PREFERRED EMBODIMENT

Figure 1:
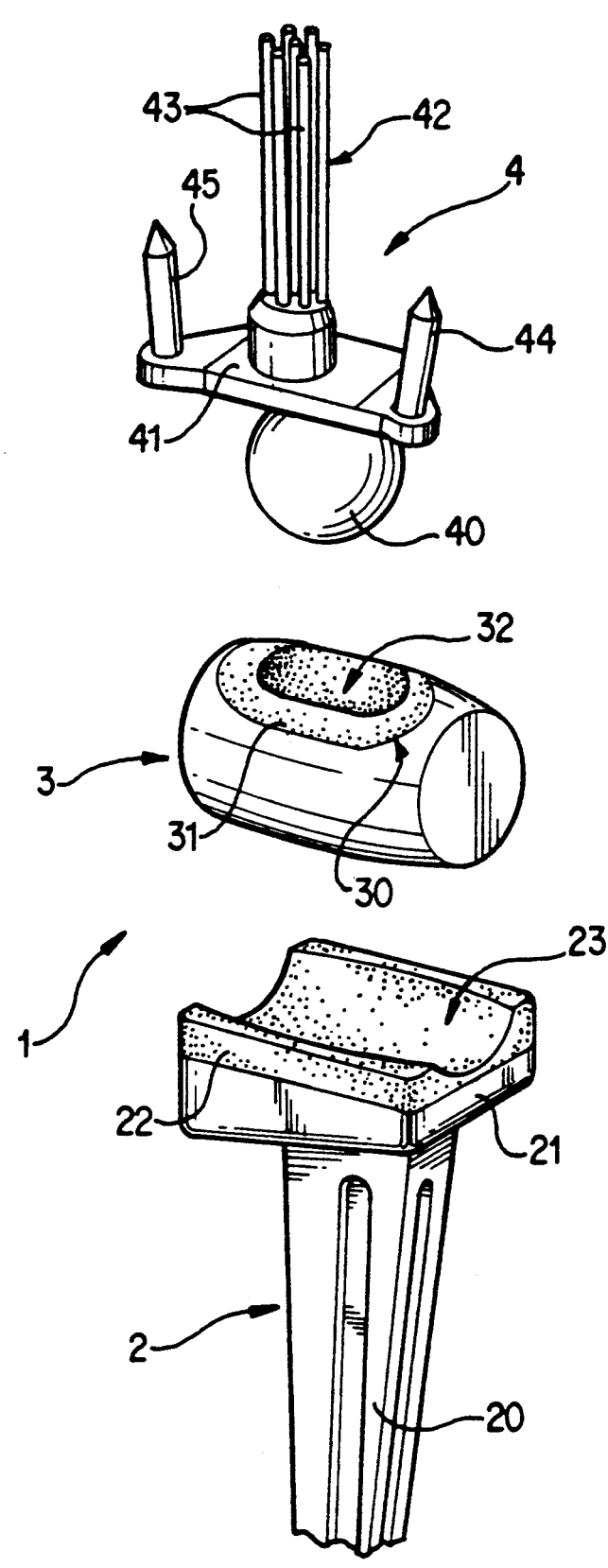
FIG. 1 is an exploded view in perspective illustrating the different elements of the wrist prosthesis according to the invention.

FIG. 1 shows a total prosthesis 1 of the wrist, comprising three elements 2, 3 and 4 articulated in one another to perfectly reproduce the two articulation movements of the wrist.

The first element 2 comprises an anchoring shank 20 in elongated form adapted to the internal morphology of the radius and a plate 21 attached to the shank which abuts against the osseous section of the radial articular surface, as will be seen more readily hereinafter.

Element 2 is made of a metallic material so that the surface of the anchoring shank 20 may be shaped allowing positioning, either with cement or without cement, inside the radial diaphysis.

Plate 21 is covered with a plate 22 which may be either integral with, or added to, element 2. Plate 22 is manufactured from a plastic material such as polyethylene or the like intended to produce the concave radio-carpal slide surface 23. To that end, the surface 23 presents a concave outer profile along its two principal axes.

The second element 3 is in the form of a conical barrel in order to perfectly cooperate with the surface 23 of the plate 22. The configuration of the barrel is such that, in its frontal plane, it is defined by an arc of a circle with a radius greater than that provided in its sagittal plane.

Figure 2:
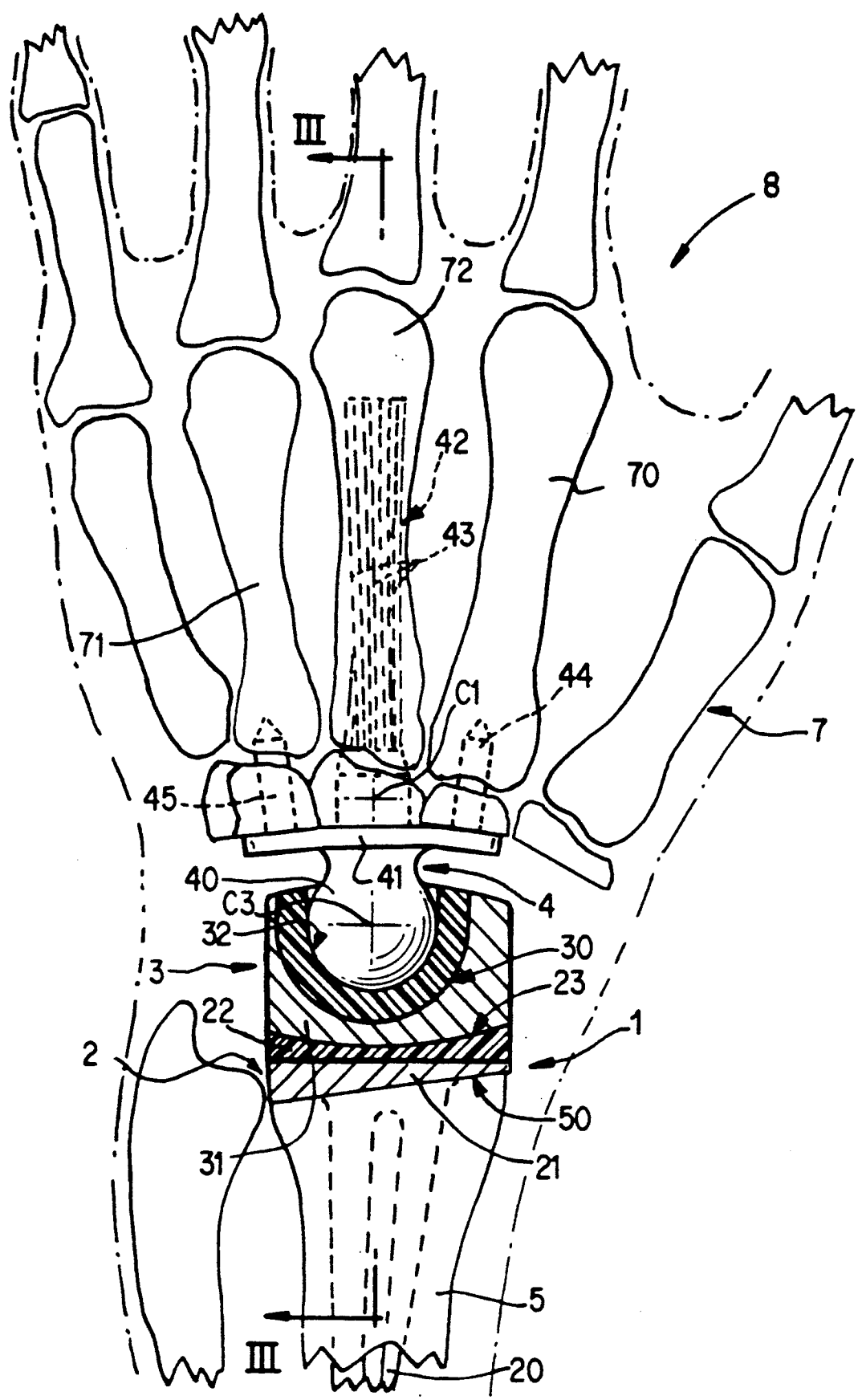
FIG. 2 is a partly sectioned, plan view showing the resection made on the radius and on the first and second rows of the carpus of a left hand for positioning the prosthesis of FIG. 1.
Figure 3:
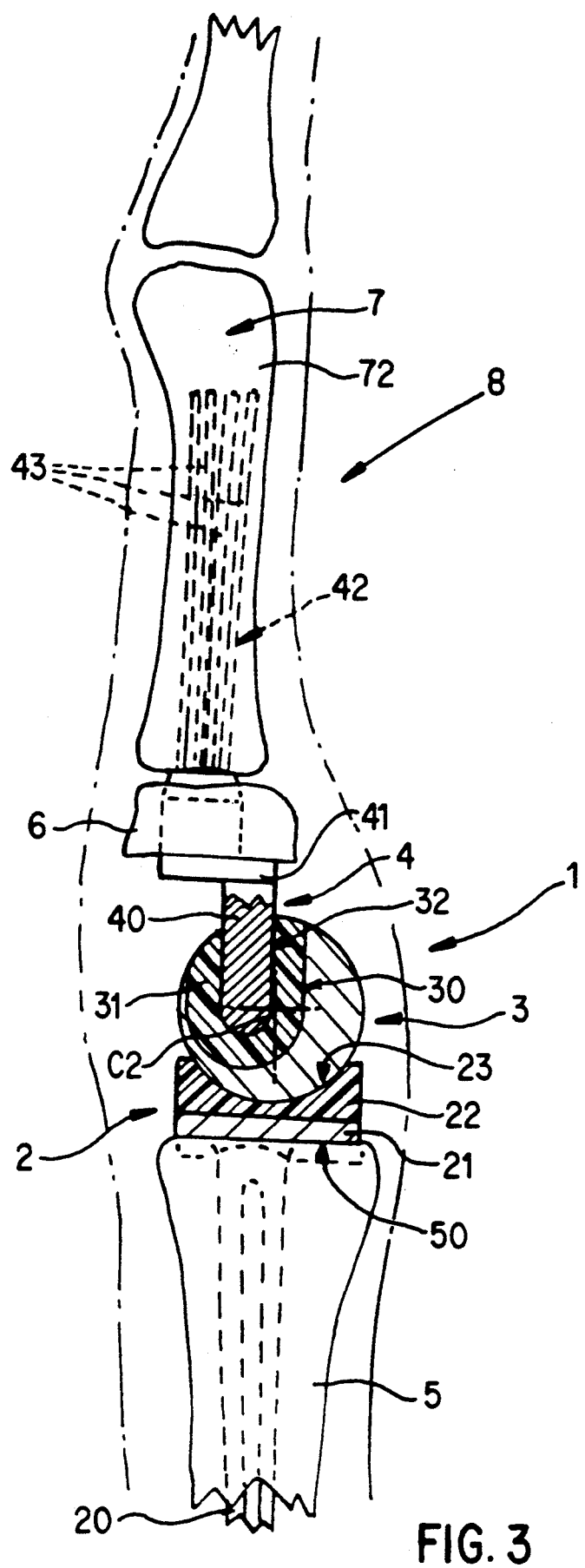
FIG. 3 is a section along III—III (FIG. 2) showing the angular shift in the sagittal plane between the fixed part and the movable parts of the prosthesis according to the invention.

In this way, at the radio-carpal articular level, the second element 3 has a first center of rotation "C1" in radio-ulnar deviation in the frontal plane (FIG. 2), which is different from a second center of rotation "C2" in flexion-extension in the sagittal plane (FIG. 3). Due to the obliqueness of the radio-carpal space, the element 3 comprises an oblique generating line to reestablish the anatomy.

An oblong recess 30 is made in element 3 so as to be laterally offset in the frontal plane either to the right or to the left depending on the anatomy of the articulation of the wrist and of the hand (FIG. 2). Moreover, it will be noted that the recess 30 is displaced upwardly in the sagittal plane of the hand (dorsal direction) so as to recover the angular shift existing between the radius 5, the carpal bones 6 and the metacarpals 7 (FIG. 3).

In addition, the upward displacement of the recess 30 gives the element 3 a function identical to that of the lunate bone, in which the center of rotation of the head of the capitate bone is offset dorsally with respect to the radio-ulnar center of rotation.

Inside the recess 30 an insert 31 made of a material such as polyethylene or the like is introduced by force. This insert includes, at its center, an oblong opening 32 making it possible to produce the medio-carpal slide surface.

This slide surface is designed to receive a third element 4 articulated so as to constitute a rotation located in the frontal plane of the wrist, i.e. from left to right and inversely in the frontal plane of the hand 8 (FIG. 2). The center "C3" of this rotation provided in the frontal plane corresponds to the center "C2" of the recess 30 of the element 3 which is offset dorsally with respect to the radio-carpal articular center of rotation "C1" described previously. Element 4 essentially includes a thick metal disc 40 which is introduced in the oblong opening 32 of the second element 3 in order to effect the rotation included in the above-mentioned frontal plane of the wrist. The disc 40 is attached to a slightly curved plate 41 which is offset dorsally with respect to the pivot plane of the disc inside the oblong opening 32 (FIG. 3).

A shank 42 composed of a bundle of flexible metal strands 43 extends from the central portion of plate 41. On either side of the shank are fixed two rigid barbs or pins 44 and 45. These barbs or pins may possibly be replaced by screws passing, or not, through expansion plugs.

FIGS. 2 and 3 show the total prosthesis of the wrist 1 of a left hand 8. It will be noted that, for positioning the prosthesis 1, the end of the radius 5 must be reshaped at 50 for the plate 21 attached to the shank 20 of the first element 2 to come into complimentary abutment with the radius 5. The inclination of the plate 21 obviously depends on the positioning of the prosthesis 1 in a left hand 8 or in a right hand, as illustrated in the Figures. The surgeon then proceeds with eliminating the proximal row of the carpus and of part of the distal row of the carpus 6. The elimination of the proximal row of the carpus allows the second element 3 to be positioned to reproduce the radio-carpal articulation of the wrist. Inside the oblong opening 32 provided in the element 3 is introduced the thick disc 40 of the third element 4 so that the barbs or pins or screws 44 and 45 are anchored in the remaining part of the distal row of the carpus 6 and in the metacarpals 70 and 71 located on either side of the middle finger 72. Inside the metacarpal diaphysis of the middle finger 72 is introduced shank 42 which includes the bundle of metal strands 43. The bundle of strands may be adapted, depending on the length and width of the diaphysis, by cutting a certain number of strands 43 with pliers. The positioning of the third element 4 makes it possible to produce the medio-carpal articulation of the wrist. In FIG. 3 it will be noted that the axis of movement of the third element 4 providing the medio-carpal articulation is offset dorsally with respect to the axis of movement of the second element 3. This shift thus allows the element 4 to effect a movement of flexion-extension close to the anatomy, as generated by the scaphoid and lunate bones, of a healthy wrist. Furthermore, it will be noted that the total prosthesis of the wrist 1 according to the present invention allows, because of the two slide surfaces, a great freedom of movements.

It will be noted that element 3 is not connected to any oseous or ligamentous structure and presents at least two degrees of freedom in rotation with respect to the radial element 2. Moreover, this, combined with the fact that the radio-carpal and medio-carpal centers of rotation are distinct, allows the medio-carpal center of rotation to be positioned or move by itself within the limit of its degrees of freedom, as a function of the stresses imposed by the anatomical structures remaining in place.

I claim:

1. A total wrist prosthesis configured to replace the lunate and scaphoid bones and which is anchored between the radius bone and metacarpal bones of an individuals hand, the prosthesis having a radio-carpal articular level and a medio-carpal articular level, with said radio-carpal articular level having a first radio-ulnar center of rotation located in a frontal plane and said medio-carpal articular level having a second radio-ulnar center of rotation located also in said frontal plane, said second radio-ulnar center of rotation being distinct from said first radio-ulnar center of rotation, said prosthesis comprising:

a radial element having an anchoring shank and a shoulder connected to said anchoring shank, said anchoring shank being configured to be inserted into a the radius bone with said shoulder resting against a distal face thereof;

a plate of bio-compatible plastic material connected to said radial element, said plate having a concave bearing surface, said concave bearing surface having a radio-ulnar deviation radius of curvature in the frontal plane and a flexion-extension radius of curvature in a sagittal plane smaller than said radio-ulnar deviation radius of curvature;

an intermediate element free to rotate in radio-ulnar deviation and in flexion-extension with respect to said concave bearing surface of the said plate according to the radio-carpal articular level of movement of the wrist, said intermediate element having a shape so as to cooperate with said concave bearing surface of said plate and including a recess, said recess being offset dorsally and in an ulnar direction;

a metacarpal element having anchor means configured to anchor into the metacarpal bones, said metacarpal element being free to rotate in a radio-ulnar deviation movement with respect to said intermediate element according to the medio-carpal articular level of movement of the wrist.

2. The total wrist prosthesis of claim 1, wherein an insert made of bio-compatible plastic material is fixed into said recess of said intermediate element.

3. The total wrist prosthesis of claim 2 wherein the metacarpal element comprises in combination:

a thick disc pivoted solely in a plane of radio-ulnar deviation inside said insert, a plate means perpendicular to said plane of radio-ulnar deviation, a shank fixed perpendicularly to said plate means opposite said thick disc and offset dorsally relative to said thick disc, said shank having a bundle of flexible metallic strands, and at least one of said anchor means placed on either side of said shank.

* * * * *